(12) United States Patent
Chu et al.

(10) Patent No.: US 6,257,046 B1
(45) Date of Patent: Jul. 10, 2001

(54) METHOD AND APPARATUS FOR DETERMINING ELECTROSTATIC FORCE PRESENT IN AN OBJECT

(75) Inventors: Wei-Cheng Chu, Ilan; Yii Feng Huang, Tainan Hsien; Kun-Sheng Teng, Tainan; Yu-Fen Wang, Kaohsiung Hsien, all of (TW)

(73) Assignee: Kang Na Hsiung Enterprise Co., Ltd., Tainan Hsien (TW)

( * ) Notice: Subject to any disclaimer, the term of this patent is extended or adjusted under 35 U.S.C. 154(b) by 0 days.

(21) Appl. No.: 09/444,836

(22) Filed: Nov. 22, 1999

(51) Int. Cl.⁷ ..................................................... G01N 3/56
(52) U.S. Cl. ................................................................... 73/7
(58) Field of Search .................................. 73/7, 8, 9, 10, 73/865.3, 432.1

(56) References Cited

U.S. PATENT DOCUMENTS

| | | | |
|---|---|---|---|
| 3,828,250 | * 8/1974 | Buser et al. | 324/72 |
| 3,835,380 | * 9/1974 | Webb | 324/72 |
| 3,898,001 | * 8/1975 | Hardenbrook et al. | 399/73 |
| 4,983,923 | * 1/1991 | Taniguchi | 324/454 |
| 5,682,102 | * 10/1997 | Takahashi et al. | 324/545 |

* cited by examiner

Primary Examiner—Max Noori
(74) Attorney, Agent, or Firm—Dickinson Wright PLLC

(57) ABSTRACT

A method for determining an electrostatic force present in a flat object, includes: (a) positioning the object on a flat support; (b) providing a series of testing membranes which are substantially free of electrostatic charges and have different standardized weights; (c) placing on the surface of the object one of the testing membranes and turning the support to an inclined position relative to a horizontal plane; (d) repeating step (c) with the other ones of the testing membranes; (e) examining which one of the testing membranes slides relative to the object after the support is inclined, and determining the smallest weight among the standardized weights, that permits a sliding movement between the testing membranes and the object, and the largest weight among the standardized weights, that prevents the sliding movement; and (f) evaluating the electrostatic force as a function of the largest weight and the smallest weight. An apparatus for carrying out the process is also disclosed.

16 Claims, 2 Drawing Sheets

METHOD AND APPARATUS FOR DETERMINING ELECTROSTATIC FORCE PRESENT IN AN OBJECT

BACKGROUND OF THE INVENTION

1. Field of the Invention

This invention relates to a method and apparatus for determining the electrostatic force present in an object, more particularly to a method and apparatus in which the electrostatic force is determined in terms of the weight of standardized testing membranes.

2. Description of the Related Art

Fibrous materials, such as non-woven fabrics, used as filter media in air filters, respirators or the like are electrostatically charged for efficient collection of dusts and other microparticles. The dust collecting properties of such a filter medium depends on the sufficiency of the electrostatic force present therein. Electrostatic force is however unfavorable for fibrous materials which are used as absorbent materials in diapers, feminine hygiene products, etc., and should be removed or reduced to a minimum. It is therefore important for manufacturers to evaluate or inspect the level of electrostatic force present in such fibrous materials in order to ensure good quality of their products.

Generally, expensive electrical instruments are used in conventional methods of measuring electrostatic forces. In an example of these methods, a capacitor-type probe is used as a detector for detecting electrostatic charges, and the detected signals are converted and amplified via additional electronic parts. While the instrument used in this method is sensitive and can provide accurate results, the construction thereof is complicated and the results thereof can be readily influenced by the surrounding conditions, such as the temperature, humidity, and the distance between the probe and the article to be tested. It is not economical to use such an instrument for testing and inspecting the electrostatic forces of products which are mass-produced and which do not require accuracy.

SUMMARY OF THE INVENTION

An object of the present invention is to provide simple and inexpensive method and apparatus for determining an electrostatic force present in an article.

Another object of the present invention is to provide an approximate evaluation method which is however reliable for determining an electrostatic force present in an object.

According to one aspect of the present invention, a method for determining an electrostatic force present in a flat object such as a fabric, includes: (a) positioning the object on a flat support; (b) providing a series of testing membranes which are substantially free of electrostatic charges and have different standardized weights; (c) placing on the surface of the object one of the testing membranes and turning the support to an inclined position relative to a horizontal plane; (d) repeating step (c) with the other ones of the testing membranes; (e) examining which one of the testing membranes slides relative to the object after the support is inclined, and determining the smallest weight among the standarized weights, that permits a sliding movement between the testing membranes and the object, and the largest weight among the standarized weights, that prevents the sliding movement; and (f) evaluating the electrostatic force as a function of the largest weight and the smallest weight.

According to another aspect of the invention, an apparatus for determining an electrostatic force present in a flat object, comprises a turnable support having a flat face and a positioning means adapted to position the object on the support, and a series of testing membranes adapted to be placed on the surface of the object held on the support, the testing membranes being substantially free of electrostatic charges and having different standardized weights.

According to still another aspect of the present invention, a method for determining an electrostatic force present in a fabric, comprises: a) positioning the fabric on a flat support; (b) placing on the surface of the fabric a testing membrane which is substantially free of electrostatic charges and which has a standarized weight; (c) turning gradually the support to an inclined position relative to a horizontal plane; (d) measuring the angle of inclination of the support which causes the testing membrane to start to slide downward relative to the fabric; and (e) evaluating the electrostatic force as a function of the weight of the testing membrane and the angle of inclination.

BRIEF DESCRIPTION OF THE DRAWINGS

Other features and advantages of the present invention will become apparent in the following detailed description of the preferred embodiment with reference to the accompanying drawings, of which.

DETAILED DESCRIPTION OF THE PREFERRED EMBODIMENTS

Figure 1:
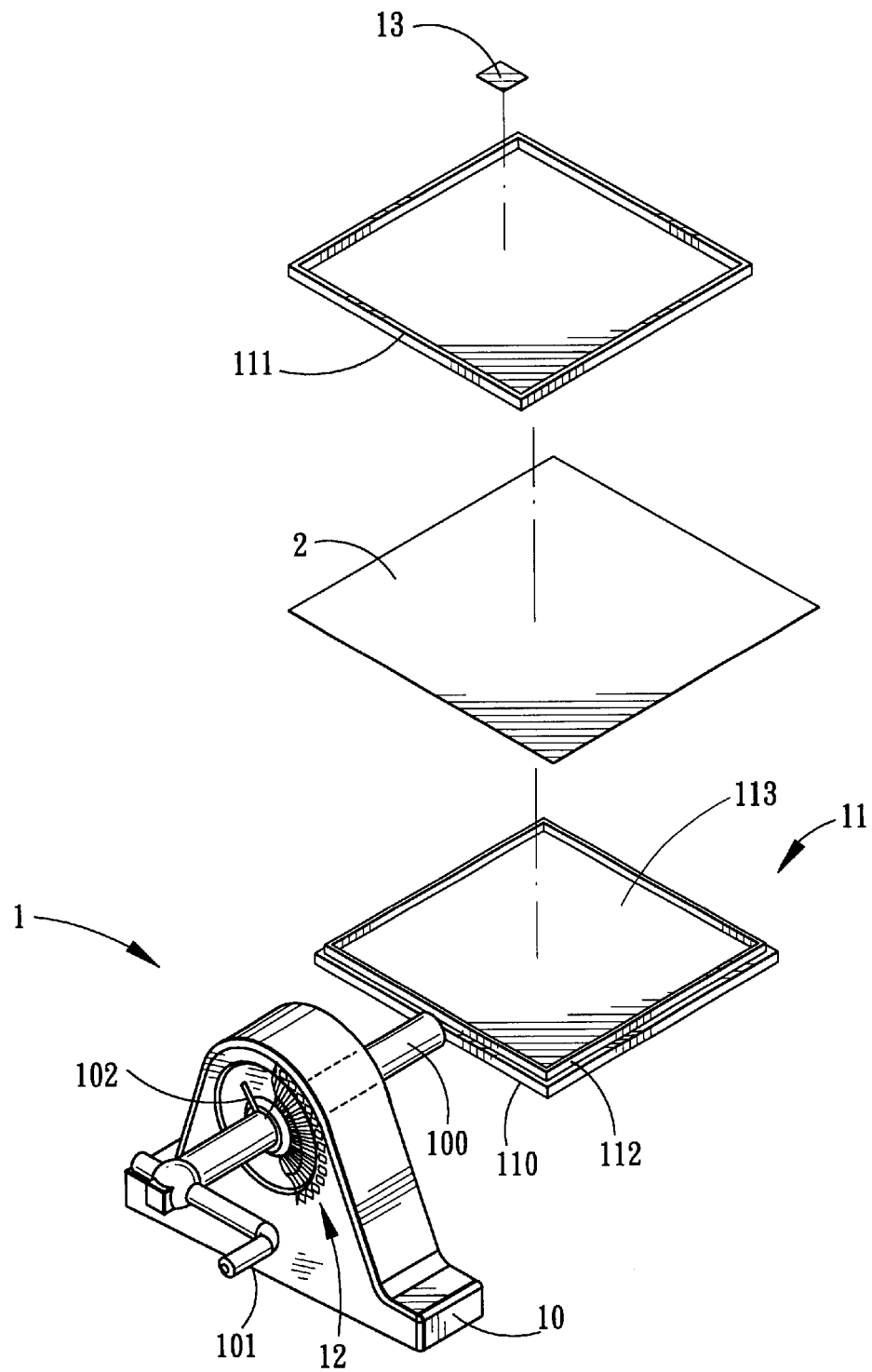
FIG. 1 is an exploded view of an apparatus for determining the electrostatic force of an object according to the present invention.
Figure 2:
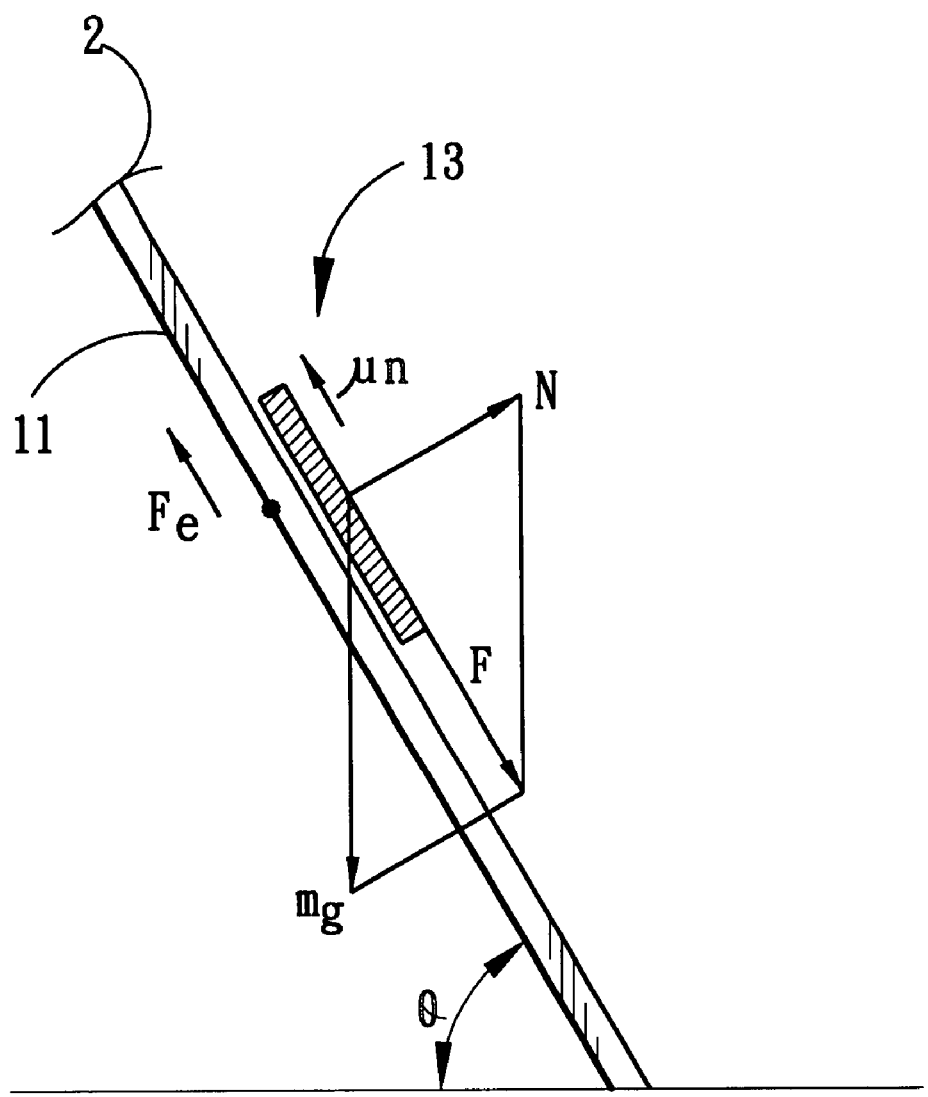
FIG. 2 illustrates an analysis of the forces acting on the testing membrane when placed on the support of the apparatus of FIG. 1.

Referring to FIGS. 1 and 2, an apparatus embodying the present invention for determining the electrostatic force present in an object, particularly a flat object such as a sheet material or a fabric is shown. The apparatus include a rotating mechanism 1, a sample support 11, an angle indicator 12 and a plurality of standarized testing membranes 13 (only one is shown).

The rotating mechanism 1 is portable and includes a base 10, and a horizontal shaft 100 which extends through the base 10 and mounted rotatably thereon. One end of the shaft 100 is connected to a lever handle 101, while the other end thereof is connected to the sample support 11. The sample support 11 can be turned by rotating the shaft 100 via the lever handle 101 so that the sample support 11 is inclined to an angle of inclination relative to a horizontal plane.

The sample support 11 includes a rectangular flat body 110 which has a flat surface 113 and a first looped member 112 projecting laterally from the flat surface 113 as a raised rim, and a second looped member 111 for fitting snugly over the first looped member 112. A fabric sheet 2 to be tested can be stretched over the flat body 110 and positioned relative thereto by being clamped between the first and second looped members 112, 111.

An angle scale 2 is disposed on the base 10 around the shaft 100, and a pointer 102 is attached radially to the shaft 100 to indicate an angle of inclination of the sample support 11 with respect to a horizontal plane.

The testing membranes 13 are rectangular thin sheets which have different standardized weights and smooth surfaces. The testing membranes are made of a low friction polymeric material that is free of electrostatic charges.

According to the present invention, the electrostatic force present in the fabric sheet 2 is determined by using the apparatus shown in FIG. 1. Firstly, one of the testing membranes 13 is placed on the fabric sheet 2 which is positioned on the sample support 11 as described hereinbefore. Then, the lever handle 101 is turned to incline gradually the sample support 11.

As shown in FIG. 2, when the angle of inclination of the sample support 11 is θ, the normal force acting on the testing membrane 3 having a weight mg is N (N=mg×cos θ), the sliding force thereof is F (F=mg×sin θ), and the friction force is $\mu$N which is opposite to the sliding force F, where $\mu$ is the friction coefficient between the testing membrane 13 and the fabric sheet 2. As the fabric sheet 2 has electrostatic charges, the testing membrane 13 would experience an electrostatic force Fe due to the charges in the fabric sheet 2. This electrostatic force Fe is also opposite to the sliding force F of the testing membrane 13. Thus, the sliding force F is counteracted by both the electrostatic force Fe and the friction force $\mu$N.

The testing membrane 3 will fall off from or slide downward relative to the fabric sheet 2 when the sliding force F is greater than the sum of the electrostatic force Fe and the friction force $\mu$N. In other words, if the electrostatic force Fe plus the friction force $\mu$N is greater than the sliding force F, the testing membrane 13 would not slide relative to the fabric sheet 2. The sliding force F of the testing membrane 3 increases as the angle of inclination θ of the sample support 11 becomes large. If the angle θ is 90°, both the normal force N and the friction force $\mu$N are zero. In this situation, only the electrostatic force Fe would act against the sliding force. In view of the aforesaid, the electrostatic force Fe has a relationship with the frictional force $\mu$N and the sliding force F. In the present invention, the electrostatic force Fe is evaluated as a function of the weight mg of the testing membrane 13 and the angle of inclination θ of the support 11 because both the sliding force F and the frictional force $\mu$N are the function of the weight mg and the angle of inclination θ.

In a method according to the present invention, after the fabric sheet 2 and the testing membrane 3 are placed on the sample support 11, the sample support 11 is inclined from a horizontal position to an appropriate inclining angle between 0 to 90°, preferably 45 to 90°. If the testing membrane 3 does not slide relative to the fabric sheet 2, it is replaced with the next testing membrane 3 having a greater weight. Whether each testing membrane 3 is at rest or slides on the fabric sheet 2 is examined so as to determine the smallest weight mg that permits the testing membrane 3 to slide and the largest weight mg that prevents the testing membrane 3 from sliding. The magnitude of the electrostatic force Fe is expressed in terms of a weight less than the aforesaid smallest weight and greater than the aforesaid largest weight of the testing membranes 3.

In an embodiment of this method, the flat surface 113 of the support 11 has an area of about 12 cm×12 cm. The testing membranes 13 are treated with an aqueous volatile solution such as an alcohol, so as to ensure that the testing membranes 13 are free of electric charges. The testing membranes 13 are prepared from a thermoplastic film and have different thicknesses. The area of each membrane 13 is 1 cm$^2$. The standarized weights of the membranes 13 are the basis weights of the membranes 13, which ranges from 1 g/m$^2$ to 500 g/m$^2$, particularly, 1 g/m$^2$, 2 g/m$^2$, 5 g/m$^2$, 10 g/m$^2$, 25 g/m$^2$, 40 g/m$^2$, 60 g/m$^2$, 80 g/m$^2$, 100 g/m$^2$, 125 g/m$^2$, 150 g/m$^2$, 200 g/m$^2$, 250 g/m$^2$, 300 g/m$^2$, 400 g/m$^2$, and 500 g/m$^2$. The angle of inclination θ is set to 60°. Assuming that there is a sliding movement between the testing membrane 3 and the fabric sheet 2 when the testing membrane 3 with 60 g/m$^2$ is placed on the fabric sheet 2 and that no sliding is observed when the 40 g/m$^2$ testing membrane 3 is on the fabric sheet 2, the electrostatic force Fe between the testing membrane 3 and the fabric sheet 2 is determined as falling between 40/m$^2$–60/m$^2$ and is expressed in terms of the range of 40–60.

According to the present invention, a second method is available for determining the electrostatic force Fe of the fabric sheet 2. In this method, the coefficient of friction $\mu$ between the testing membrane 3 and the fabric sheet 2 is firstly determined by conducting a test on a reference fabric sheet which is the same material as the fabric sheet 2 but is treated to be free of electrostatic charges. The reference fabric sheet is mounted on the support 11, and one of the testing membranes 13 is placed on the fabric sheet. The support 11 is turned to an inclined position relative to a horizontal plane. When the testing membrane 13 starts to slide, the angle of inclination θ indicated by the pointer 102 is read. The weight of the testing membrane 13 is known. The coefficient of friction $\mu$ between the reference fabric sheet and the testing membrane 13 is calculated from the following equation:

$$F = mg \times \sin\theta = \mu N + Fe \qquad (1)$$
$$= \mu(mg \times \cos\theta) + Fe$$

As the reference fabric sheet is free of electrostatic charges, Fe is zero, and the equation (1) becomes:

$$F = mg \times \sin\theta = \mu(mg \times \cos\theta). \qquad (2)$$

The friction coefficient $\mu$ between the testing membrane 13 and the reference fabric sheet (or the fabric sheet 2) is obtained from equation (2).

An additional test is conducted on the fabric sheet 2 by replacing the reference fabric sheet with the fabric sheet 2 to be tested on the support 11 and placing the same testing membrane 13 on the fabric sheet 2, following the previous procedure to determine the angle θ. The electrostatic force of the fabric sheet 2 is calculated from the following equation (3) which is derived from equation (1):

$$Fe = mg(\sin\theta - \mu\cos\theta) \qquad (3)$$

where $\mu$ is the value obtained from equation (2).

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

What is claimed is:

1. A method for determining an electrostatic force present in a flat object, comprising:

(a) positioning the object on a flat support;

(b) providing a series of testing membranes which are substantially free of electrostatic charges and have different standarized weights;

(c) placing on the surface of the object one of the testing membranes and turning the support to an inclined position relative to a horizontal plane;

(d) repeating step (c) with the other ones of the testing membranes; and (e) examining which one of the testing membranes slides relative to the object after the support is inclined, and determining the smallest weight among the standarized weights, that permits a sliding movement between the testing membranes and the object, and the largest weight among the standarized weights, that prevents the sliding movement; and (f) evaluating the electrostatic force as a function of the largest weight and the smallest weight.

2. The method according to claim 1, wherein the support is turned to an angle of about 45°–90°.

3. The method according to claim 1, wherein the electrostatic force is expressed in terms of a range between the largest weight and the smallest weight.

4. An apparatus for determining an electrostatic force present in a flat object, comprising:

a support having a flat face and a positioning means adapted to position the object on the flat face of the support, the support being turnable to place the flat face in an inclined position that includes the object; and a series of testing membranes substantially free of electrostatic charges and having different standarized weights, the testing membranes being adapted to be selectively placed on the surface of the object held on the support so as to determine the smallest one of the standarized weights, that permits a sliding movement between the corresponding one of the testing membranes and the object, and the largest one of the standarized weights that prevents the sliding movement between the corresponding one of the testing membranes and the object, whereby the electrostatic force present in the object is evalutated as a function of the smallest one and the largest one of the standarized weights.

5. The apparatus according to claim 4, wherein said testing membranes have a smooth surface adapted to contact the surface of the object.

6. The apparatus according to claim 4, wherein said testing membranes are made of a polymeric material.

7. The apparatus according to claim 4, wherein the testing membranes are made of the same material and have the same surface area and different thicknesses.

8. The apparatus according to claim 7, wherein the testing membranes have a series of basis weights ranging from 1 g/m² to 500 g/m², the basis weights being used as the standarized weights.

9. The apparatus according to claim 8, wherein the testing membranes have an area of 1 cm².

10. The apparatus according to claim 4, further comprising a rotating mechanism connected to the support for turning the support.

11. The apparatus according to claim 10, further comprising an angle indicator associated with the rotating mechanism to indicate an angle of inclination of the support.

12. The apparatus according to claim 4, wherein the positioning means includes first and second looped members for fitting snugly one over another, the first and second looped members being separable from one another and adapted to clamp the object therebetween.

13. The apparatus according to claim 12, wherein the support has a flat body, the first looped member being integrally formed with the support and projecting laterally from the flat body as a looped rim, the second looped member being separately formed relative to the support.

14. The apparatus according to claim 13, further comprising a rotating mechanism for changing the angle of inclination of the support, said rotating mechanism including a seat, a horizontal shaft journalled in said seat, and a turning handle connected to the shaft at one side of the seat, the flat body being connected to the shaft at the other side of the seat.

15. The apparatus according to claim 14, further comprising an angle scale disposed on the seat around the shaft, and a pointer connected to the shaft adjacent to the angle scale.

16. A method for determining an electrostatic force present in a fabric, comprising:

(a) positioning the fabric on a support;

(b) placing on a surface of the fabric a testing membrane which is substantially free of electrostatic charges and which has a standarized weight;

(c) turning gradually the support to an inclined position relative to a horizontal plane;

(d) measuring the angle of inclination of the support which causes the testing membrane to start to slide downward relative to the surface of the fabric; and (e) evaluating the electrostatic force as a function of the weight of the testing membrane and the angle of inclination.

\* \* \* \* \*